United States Patent
Joshi et al.

(10) Patent No.: US 6,436,992 B1
(45) Date of Patent: Aug. 20, 2002

(54) USE OF FUMARIC ACID DERIVATIVES

(75) Inventors: Rajendra Kumar Joshi, Zürich; Hans Peter Strebel, Muri, both of (CH)

(73) Assignee: Fumapharm AG, Muri (CH)

( * ) Notice: Subject to any disclaimer, the term of this patent is extended or adjusted under 35 U.S.C. 154(b) by 0 days.

(21) Appl. No.: 09/194,862

(22) PCT Filed: Apr. 1, 1998

(86) PCT No.: PCT/EP98/01894

§ 371 (c)(1),
(2), (4) Date: Jul. 8, 1999

(87) PCT Pub. No.: WO98/52549

PCT Pub. Date: Nov. 26, 1998

(30) Foreign Application Priority Data

May 20, 1997 (DE) .......................................... 197 21 099

(51) Int. Cl.⁷ ....................... A61K 31/225; A61K 31/22

(52) U.S. Cl. ................... 514/547; 514/546; 514/549

(58) Field of Search ................................ 514/547, 546, 514/549

(56) References Cited

U.S. PATENT DOCUMENTS 4,959,389 A * 9/1990 Speiser et al. ............... 514/494

FOREIGN PATENT DOCUMENTS

| CN | 941 191 48 | 6/1996 | .......... A61K/38/13 |
|---|---|---|---|
| DE | 26 21 214 | 11/1977 | .......... A61K/31/215 |
| DE | 35 31 597 | 3/1987 | .......... A61K/45/02 |
| EP | 312 697 | 4/1989 | .......... A61K/31/225 |
| EP | 0 312 692 | * 4/1993 | .......... A61K/31/225 |
| EP | 793 966 | 9/1997 | .......... A61K/38/13 |
| GB | 2 291 422 | 1/1996 | .......... C07N/471/04 |
| WO | WO96/01122 | 1/1996 | .......... A61K/38/20 |
| WO | WO960890 A1 | 3/1996 | .......... A01N/13/00 |

OTHER PUBLICATIONS

"Immunmodulation durch Fumaderm", Symposium, with partial translation, Chanite–Berlene Haulkluli Nov. 1, 1996–Nov. 3, 1996.

Article entitled "A Defective Purine Nucleotide Synthesis Pathway in Psoriatic Patients" by R. Kiehl, et al., dated Aug. 1992 taken from Acta Derm. Venerol, No. XP–002088945, pp. 253–255.

Article entitled "Effect of Fumaric Acid, Its Dimethylester, and Topical Antipsoriatic Drugs on Epidermal Differentiation in the Mouse Tail Model", by B. Seök, et al., taken from Skin Pharmacology, dated Mar. 1996, No. XP–002088946, pp 99–103.

Article entitled "Contact urticaria from Diethyl fumarate" by Arto Lahti, et al., taken from Contact Dermatitis, dated Mar. 1985, No. XP–002088947, pp. 139–140.

Article entitled "Osteomalazie als offenbar seltene Nebenwirkung der oralen Fumarsäuretherapie" by Lothar Filegner, et al., taken from Hautarzt, dated Sep. 1992, No. XP002088948, pp. 554–560.

Article entitled "Nephrotoxische Wirkung von Fumarsäurederivaten" by A. Sadjak, et al., taken from Deutsch Med. Wochenschr, No. XP–002088949, dated Mar. 22, 1991, p. 478.

Article entitled "Acetysalicylic acid inhibits non–immunologic contact urticaria" by Arto Lahti, et al., taken from Contact Dermatitis, dated Mar. 3, 1987, No. XP–002088950, pp 133–135.

Article entitled "Zwei Fälle von Nebenwirkungen einer Fumarsäreester–Lokaltherapie", by P. Dücker, et al., taken from H+G Zeischrift für Haukrankheiten, dated Aug. 1990, No. XP–002088951, pp 734–736.

Article entitled "Fumaric acid therapy in psoriasis: Results and side effect of 2 years of treatment" by Dinanda N. Kolbach, et al., dated Nov. 1992, taken from J. American Acady of Dermatology, No. XP–002089560, pp 769–771.

Article entitled "Dimethylfumarate Is an Inhibitor of Cytokine–Induced E–Selectin, VCAM–1, and ICAM–1 Expression in Human Endothelial Cells" by Marc Vandermeeren, et al., dated Mar 8, 1997, taken from Biochemical and Biophysical Research Communication, No. XP–002089561, pp 19–23.

Article entitled Systemic therapy with fumaric acid derivates: New possibilites in the treatment of psoriasis, by C. Nieboer, et al., dated Apr. 8, 1990, No. XP–002089562, pp. 601–608.

Article entitled "Fumaric Acid Esters (FAEs) Suppress CD 15–and ODP 4–positive Cells in Psoriasis" by M. Bacharach–Buhles, et al., taken Acta Derm Venereol (Stockh), 1994, pp 79–82 No. XP–002088940.

Article entitled "Psoriasis, eine Autoimmunkrankheit?" by Th. Hunziker, et al., taken from Therapeutisch Umscham, No. XP–002088941, p 110–113.

Article entitled "The antipsoriatic agent dimethylfumarate immunomodulates T–cell cytokine secretion and inhibits cytokines of the psoriate cytokine network" by H.M. Ockenfels, et al., taken from British Journal of Dermotology, dated 1998, No. XP–002089713, pp 390–395.

Article entitled "Perorale Langzeitbehandlung der Psoriasis mit Fumarsäurederivaten" by Walter Bayard, et al., taken from Her Hautrtz, dated 1997, pp 279–285.

(List continued on next page.)

*Primary Examiner*—Russell Travers
(74) *Attorney, Agent, or Firm*—Cohen, Pontani, Lieberman & Pavane

(57) ABSTRACT

Disclosed is a method of treating auto-immune diseases by the administration of certain fumaric acid monoalkyl esters as salts or free acids thereof either alone or in combination with a dialkyl fumarate.

23 Claims, No Drawings

OTHER PUBLICATIONS

Article entitled "Elevation of Gluthathione Levels by Phase II Enzyme Inducers: Lack of Inhibition of Human Immunodeficiency Virus Type 1 Replication in Chronically Infected Monocytoid Cells", by Hans J. Prochaska, et al., taken from Mol. Pharmacol, No. XP002088942, pp 916–921.

Article entitled "Antiproliferative and cytotoxic profiles of antipsoriatic fumaric acid derivatives in keratinocyte cultures" by Béla Sebök, et al., taken from Eur. J. Pharmacol. Article entitled "Fumaric acid derivatives evoke a transient increase in intracellular free calcium concentration and inhibit the proliferation of human keratinocytes" by H.B. Thio, et al., taken from British Journal of Dermatology, dated Dec. 1994, No. XP–002088944, pp 856–861.

Article taken from "Der Hautarzi" published by Springer–Verlag 1987 entitled "Perorale Langzeitbehandllung der Psoriasis mit Fumarsäurederivarten" written by Walter Baynard,, pp 279–285.

Mar. Index 10$^{th}$ Ed 1983 Abstract 2748.*

Hunziku et al Acta Derm Venenol (Stockl.) 1994 Suppl 1868–79–82.*

Therapeutische Umcschan, Bend 50, Heltz pp 110–113, 1993.*

Sebok et al, European J of Pharmacology vol. 270 pp 79–87, 1994.*

* cited by examiner

USE OF FUMARIC ACID DERIVATIVES

This Application is a 371 of PCT/EP98/01894 filed Apr. 1, 1998 which claims priority from German Patent Application no. 197,21,099.5 filed May 20, 1997.

BACKGROUND OF THE INVENTION

The present invention relates to the use of certain fumaric acid monoalkyl esters as salt either alone or in combination with a dialkyl fumarate for preparing pharmaceutical compositions for the treatment of poly-arthritis, multiple sclerosis and graft-versus-host reactions. The invention also relates to medicaments containing one or several fumaric acid monoalkyl esters in the form of free acids, optionally in combination with dialkyl fumarate, as active ingredient for the treatment of polyarthritis, multiple sclerosis, graft-versus-host reactions and other auto-immune diseases. These compositions do not contain fumaric acid per se. The use according to the invention also extends to the treatment of juvenile diabetes, Hashimoto's thyroiditis, Grave's disease, systemic Lupus erythematosus (SLE), Sjogren's syndrome, pernicious anaemia and chronically active (=lupoid) hepatitis.

Pharmaceutical compositions which end in the citric acid cycle when decomposed after administration or which belong to the citric acid cycle are increasingly gaining therapeutic value, especially when given in high dosages, because they help relieve or heal diseases with cryptogenetic causes.

Fumaric acid, for example, inhibits the growth of the Ehrlich ascites tumour in mice, reduces the toxic effects of mitomycin C and aflatoxin [K. Kuroda, M. Akao, Biochem. Pharmacol. 29, 2839–2844 (1980)/Gann. 72, 777–782 (1981)/Cancer Res. 36, 1900–1903, (1976)] and displays a anti-psoriatic and anti-microbial activity [C. N. Huhtsnen, J. Food Sci. 48, 1574 (1983)/M. N. Islam, U.S. Pat. No. 4,346,118 dated Aug. 24, 1982/C. A. 97, 161317b (1982)].

When administered parenterally, dermally and especially perorally, high dosages of fumaric acids or its derivatives known so far such as dihydroxy fumaric acid, fumaramide and fumaronitrile have such unacceptably severe side effects and high toxicity [P. Holland, R. G. White, Brit. Dermatol. 85, 259–263 (1971)/M. Hagedorn, K. W. Kalkoff, G. Kiefer, D. Baron. J. Hug, J. Petres, Arch. Derm. Res. 254, 67–73 (1975)] that, in most cases, such a therapy had to be abandoned in the past.

European Patent Application 18 87 49 already describes fumaric acid derivatives and pharmaceutical compositions containing the same for the treatment of psoriasis. Pharmaceutical compositions for the treatment of psoriasis containing a mixture of fumaric acid and other fumaric acid derivatives are known from DE-A-25 30 372. The content of free fumaric acid is obligatory for these medicaments.

DE-A-26 21 214 describes medicaments containing the fumaric acid monoethyl ester and its mineral salts as active ingredient for the treatment of psoriasis. The publication "Hautarzt (Dermatologist) (1987) 279–285" discusses the use of fumaric acid monoethyl ester salts (Ca, Zn, Mg) and of the fumaric acid dimethyl ester for the treatment of psoriasis. Pharmaceutical compositions containing a mixture of fumaric acid monoalkyl ester salts and a fumaric acid diester for the treatment of psoriasis, psoriatic arthritis, neurodermitis and enteritis regionalis Crohn are known from EP 0 312 697 B1.

Surprisingly, we have now found in in vitro tests and in animal experiments that it is possible to treat polyarthritis, multiple sclerosis and graft-versus-host reactions with pharmaceutical compositions using one or several compounds from the group consisting of calcium, magnesium, zinc and iron salts of fumaric acid monoalkyl esters of the general formula

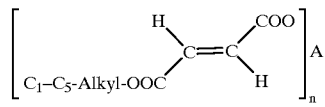

optionally in admixture with dialkyl fumarate of the formula

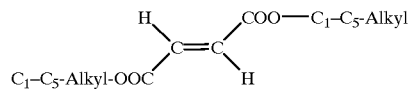

wherein A is a bivalent cation from the series consisting of Ca, Mg, Zn or Fe or a monovalent cation from the series consisting of potassium or sodium, respectively, and n denotes the numeral 1 or 2 depending on the type of cation, optionally together with commonly used pharmaceutical excipients.

We also found an effect when polyarthritis, multiple sclerosis and graft-versus-host reactions were treated with pharmaceutical compositions containing one or several compounds of alkyl hydrogen fumaric acid of the general formula

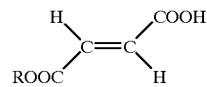

optionally in admixture with dialkyl fumarate of the formula

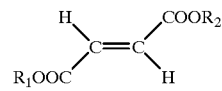

wherein R, $R_1$, $R_2$ may be the same or different and each of R, $R_1$ and $R_2$ is an alkyl group having 1 to 5 carbon atoms ($C_1$–$C_5$ alkyl);

and, optionally, commonly used pharmaceutical excipients and carriers.

Preferred compositions according to the invention contain the calcium salt of the fumaric acid monomethyl ester, the calcium salt of the fumaric acid monomethyl ester in admixture with dimethyl fumarate or the relevant salts of the fumaric acid monoethyl ester.

Preparations containing the calcium salt of the fumaric acid monoalkyl ester or the fumaric acid alkyl ester in the form of the free acid in an amount of 10 to 300 mg are especially suitable for administration, the total weight of the active ingredients being 10 to 300 mg.

Other preferred oral forms of administration contain 10 to 290 parts by weight of the calcium salt of the fumaric acid monoalkyl ester and 290 to 10 parts by weight of dimethyl fumarate as well as 1 to 50 parts by weight of the zinc salt of the fumaric acid monoalkyl ester or 1 to 250 parts by weight of the calcium salt of the fumaric acid monoalkyl ester, 250 to 10 parts by weight of dimethyl fumarate, 1 to 50 parts by weight of the magnesium salt of the fumaric acid monoalkyl ester and 1 to 50 parts by weight of the zinc salt of the fumaric acid monoalkyl ester or the monomethyl ester, respectively, the total weight of the active ingredients being 30 to 300 mg.

Preferred compositions according to the invention also contain the methyl hydrogen fumarate in an amount of 10 to 300 mg.

For commencement of a systemic therapy and, vice versa, termination of the treatment by gradual reduction of the dosage, low doses containing, for example, 30.0 mg of dimethyl fumarate, 20.0 mg of the calcium salt of monoethyl fumarate and 3.0 mg of the zinc salt of monoethyl fumarate or monomethyl fumarate, respectively, are advantageous.

For therapeutic dosing after an initial phase, for example, a dosage of 120.0 mg of dimethyl fumarate, 87.0 mg of the calcium salt of the monoethyl fumarate and 3.0 mg of the zinc salt of the mono ethyl fumarate or the monomethyl fumarate may be used.

The fumaric acid derivatives contained in the compositions according to the invention, are obtained by a) condensation of a compound of the formula

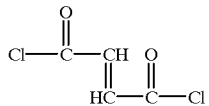

with 2 moles of alkyl alcohol (ROH) by a known method to obtain a diester, followed by controlled hydrolysation to obtain a monoester, or b) condensation of 1 mole of the relevant alkyl alcohol (ROH) in the usual manner followed by hydrolysis of the monoacid chloride thus obtained to obtain an acid, or c) direct condensation of the fumaric acid with 2 moles of alkyl alcohol (ROH) by a known method to obtain the relevant diester followed by controlled hydrolysation to obtain the monoester, or d) direct condensation of maleic acid or maleic anhydride with 1–2 moles of the relevant alkyl alcohol (ROH) by a known method to obtain a mono- or diester followed by catalytic isomerisation to obtain the respective fumaric acid derivative.

The salts of the fumaric acid monoalkyl esters may also be obtained by reacting a compound of the general formula

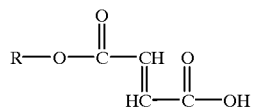

wherein R is a $C_1$–$C_5$ alkyl group with equivalent mole amounts of Na, K, Fe, Ca, Mg or Zn hydroxide or oxide in toluene and removing the water generated during the reaction.

For particularly preferred applications, preparations containing the following active ingredients in the stated dosages and proportions are used:

as a pharmaceutical composition for oral administration in the form of tablets or capsules, characterised in that they contain the calcium salt of the fumaric acid monomethyl ester in an amount of 10 to 300 mg, the total weight of the active ingredients being 10 to 300 mg; or as a pharmaceutical composition for oral administration in the form of tablets or capsules, characterised in that they contain 10 to 290 parts by weight of the calcium salt of the fumaric acid monomethyl ester and 290 to 10 parts by weight of dimethyl fumarate, the total weight of the active ingredients being 20 to 300 mg; or additionally, as a pharmaceutical composition for oral administration in the form of tablets or capsules characterised in that they contain 10 to 250 parts by weight of the calcium salt of the fumaric acid monomethyl ester, 1 to 50 parts by weight of dimethyl fumarate and 1 to 50 parts by weight of the zinc salt of the fumaric acid monomethyl ester, the total weight of the active ingredients being 20 to 300 mg, or as a pharmaceutical composition for oral administration in the form of tablets or capsules, characterised in that they contain 10 to 250 parts by weight of the calcium salt of the fumaric acid mono methyl ester, 250 to 10 parts by weight of dimethyl fumarate, 1 to 50 parts by weight of the magnesium salt of the fumaric acid monomethyl ester and 1 to 50 parts by weight of the zinc salt of the fumaric acid monomethyl ester, the total weight of the active ingredients being 30 to 300 mg, or, alternatively, as a pharmaceutical composition for oral administration which may be provided with a coating resistant to gastric acid, as a pharmaceutical preparation for the treatment of polyarthritis, multiple sclerosis or graft-versus-host reactions for peroral administration in the form of pellets, micro-tablets, capsules, granules and tablets, in the form of ointments, plasters or lotions for cutaneous and transdermal administration, in the form of aqueous micro-dispersions, oil-in-water emulsions or oily solutions for parenteral administration, or suppositories or micro-enemas for rectal administration, and as a pharmaceutical composition for the treatment of polyarthritis, multiple sclerosis or graft-versus-host reactions, characterised in that it contains one or several compounds selected from the group consisting of free acids of fumaric acid monoalkyl esters of the general formula

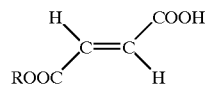

optionally in combination with dialkyl fumarate of the formula

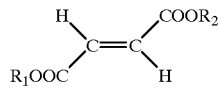

and R, $R_1$ and $R_2$ are as defined above.

and carriers, said composition not containing fumaric acid in its free form, or as a pharmaceutical composition for oral administration in the form of tablets, capsules or micro-tablets, characterised in that they contain alkyl hydrogen fumarate in an amount of 10 to 300 mg, the total weight of the active ingredients being 10 to 300 mg, or as a pharmaceutical composition for oral administration in the form of tablets, capsules or micro-tablets, characterised in that they contain 10 to 290 parts by weight of alkyl hydrogen fumarate and 290 to 10 parts by weight of dialkyl fumarate, the total weight of the active ingredients being 20 to 300 mg, or as pharmaceutical compositions containing the free acid of the fumaric acid monomethyl ester (methyl hydrogen fumarate), or as a pharmaceutical composition for oral administration in the form of tablets, capsules or micro-tablets, characterised in that they each contain the methyl hydrogen fumarate in an amount of 10 to 300 mg, the total weight of the active ingredients being 10 to 300 mg, or as a pharmaceutical composition for oral administration in the form of tablets, capsules or micro-tablets containing 10 to 290 parts by weight of methyl hydrogen fumarate and 290 to 10 parts by weight of dimethyl fumarate, the total weight of the active ingredients being 20 to 300 mg, or, as a pharmaceutical composition for the treatment of polyarthritis, multiple sclerosis or graft-versus-host reactions for peroral administration in the form of micro-pellets, micro-tablets, capsules, granulates and tablets, in the form of ointments, plasters, lotions or shower preparations for cutaneous and transdermal administration, in the form of aqueous micro-dispersions, oil-in-water emulsion or oily solutions for parenteral administration, or suppositories or micro-enemas for rectal administration.

According to a preferred form of administration, the size or mean diameter of the pellets or micro-tablets is in the range of 300 to 2,000 μm, especially in the range of 500 μm to 1,500 μm or 1,000 μm.

Another special benefit of the use according to the invention is to alternate a treatment regimen with cyclosporin sequentially with administration of the fumaric acid derivatives described above. In other words, an application of fumaric acid derivatives according to the above definitions for a period of one or several weeks could follow a cyclosporin therapy extending over one or several weeks. As a result, the well-known severe side effects of a long-term cyclosporin therapy can be reduced dramatically and unexpectedly.

In order to illustrate the use according to the invention, various examples for the preparation of preferred medicaments are given below:

PRODUCTION EXAMPLES

Example 1

Production of enteric-coated film tablets containing 100.0 mg of monoethyl fumarate-Ca salt, which corresponds to 71 mg of fumaric acid Taking the necessary precautions (breathing mask, gloves, protective clothing, etc.), 10.000 kg of monoethyl fumarate-Ca salt are crushed, mixed intensely and homogenised by means of an 800 sieve. Then an excipient mixture of the following composition is prepared: 21.000 kg of starch derivative (STA-RX 1500®), 2.000 kg of micro-crystalline cellulose (Avicel PH 101®), 0.600 kg of polyvinyl pyrrolidone (PVP, Kollidon® 25), 4.000 kg of Primogel®, 0.300 kg of colloidal silicic acid (Aerosil®).

The active ingredient is added to the entire powder mixture, mixed, homogenised by means of a 200 sieve and processed with a 2% aqueous solution of polyvinyl pyrrolidone (PVP, Kollidon® 25) in the usual manner into binder granules, and then mixed with the outer phase in a dry state. The latter consists of 2.000 kg of a so-called FST complex containing 80% of talcum, 10% of silicic acid and 10% of magnesium stearate.

Afterwards the mixture is pressed into convex tablets with a weight of 400 mg and a diameter of 10.0 mm by the usual method. Instead of these classic compaction methods, other methods such as direct compaction or solid dispersions according to the melting and spray drying method may also be used for preparing tablets.

Enteric Coating

A solution of 2.250 kg of hydroxy propyl methyl cellulose phthalate (HPMCP, Pharmacoat HP® 50) is dissolved in a solvent mixture consisting of 2.50 liters of demineralised water, 13.00 liters of acetone (Ph. Helv. VII) and 13.00 liters of ethanol (94% by weight) and then 0.240 kg of castor oil (Ph. Eur. II) added to the solution. The solution is poured or sprayed in portions onto the tablet cores in a coating pan in a conventional manner or applied by means of a fluidised bed apparatus of the appropriate structure.

After drying, the film coating is applied. Said coating consists of a solution of Eudragit E 12.5%® 4.800 kg, talcum (Ph. Eur. II) 0.340 kg, titanium(VI) oxide Cronus RN 56® 0.520 kg, coloured lacquer ZLT-2 blue (Siegle) 0.210 kg, and polyethylene glycol 6000 (Ph. Helv. VII) 0.120 kg in a solvent mixture of 8.200 kg of 2-propanol (Ph. Helv. VII), 0.060 kg of glycerine triacetate (Triacetin®) and 0.200 kg of demineralised water. After homogenous distribution in the coating pan or the fluidised bed, the mixture is dried and polished in the usual manner.

Example 2

Preparation of enteric coated capsules containing 86.5 mg of monoethyl fumarate-Ca salt and 110.0 mg of dimethyl fumarate, which corresponds to a total of 150 mg of fumaric acid Taking the necessary precautions (breathing mask, gloves, protective clothing, etc.), 8.650 kg of monoethyl fumarate-Ca salt and 11.000 kg of dimethyl fumarate are intensely mixed with a mixture consisting of 15.000 kg of starch, 6.000 kg of lactose (Ph. Helv. VII), 2.000 kg of micro-crystalline cellulose (Avicel®), 1.000 kg of polyvinyl pyrrolidone (Kollidon® 25) and 4.000 kg of Primogel® and homogenised by means of a 800 sieve.

Together with a 2% aqueous solution of polyvinyl pyrrolidone (Kollidon® 25) the entire powder mixture is processed in the usual manner into a binder granulate and mixed with the outer phase in the dried state. Said outer phase consists of 0.350 kg of colloidal silicic acid (Aerosil®), 0.500 kg of Mg stearate and 1.500 kg of talcum (Ph. Helv. VII). The homogeneous mixture is then filled in portions of 500.0 mg into appropriate capsules which are then provided with a enteric-coated coating consisting of hydroxy propyl methyl cellulose stearate and castor oil as softening agent by a known method. Instead of hard gelatine capsules, the mixture may also be filled into appropriate gastric acid-resistant capsules, which consist of a mixture of cellulose acetate phthalate (CAP) and hydroxy propyl ethyl cellulose phthalate (HPMCP).

Example 3

Preparation of enteric-coated capsules containing 203.0 mg of monoethyl fumarate-Ca salt, 5.0 mg of monoethyl fumarate-Mg salt and 3.0 mg of monoethyl fumarate-Zn salt, which corresponds to a total of 150 mg of fumaric acid Taking the necessary precautions (breathing mask, gloves, protective clothing, etc.), 20.300 kg of mono ethyl fumarate-Ca salt, 0.500 kg of monoethyl fumarate-Mg salt and 0.300 kg of monoethyl fumarate-Zn salt are crushed, mixed intensely and homogenised using an 800 sieve. A homogenous powder mixture of the following composition is mixed into this active ingredient mixture: spray-dried lactose 12.900 kg, colloidal silicic acid 1.000 kg, micro-crystalline cellulose (Avicel®) 2.000 kg, magnesium stearate (Ph. Helv. VII) 1.000 kg and talcum (Ph. Helv. VII) 2.000 kg. The entire powder mixture is homogenised once again by means of a 200 sieve, filled into hard gelatine capsules with a net weight of 400 mg and sealed. The application of a gastric acid-resistant coating is carried out in accordance with example 2.

Example 4

Preparation of enteric-coated micro-tablets in capsules containing 87.0 mg of monoethyl fumarate-Ca salt, 120.0 mg of dimethyl fumarate, 5.0 mg of monoethyl fumarate-Mg salt and 3.0 mg of monoethyl fumarate-Zn salt, which corresponds to a total of 164 mg of fumaric acid ("forte" tablets)

Taking the necessary precautions (breathing mask, gloves, protective clothing, etc.), 8.700 kg of monoethyl fumarate-Ca salt, 12.000 kg of dimethyl fumarate, 0.500 kg of monoethyl fumarate-Mg salt and 0.30 kg of monoethyl fumarate-Zn salt are crushed, intensely mixed and homogenised by means of an 800 sieve. Then an excipient mixture of the following composition is prepared: 18.00 kg of starch derivative (STA-RX 1500), 0.30 kg of micro-crystalline cellulose (Avicel PH 101), 0.75 kg of PVP (Kollidon 120)., 4.00 kg of Primogel, 0.25 kg of colloidal silicic acid (Aerosil). The entire powder mixture is added to the active ingredient mixture, homogenised by means of a 200 sieve, processed in the usual manner with a 2% aqueous solution of polyvinyl pyrrolidone (Kollidon K25) to obtain a binder granulate and mixed in a dry state with the outer phase consisting of 0.50 kg of Mg stearate and 1.50 kg of talcum. Then the powder mixture is pressed by the conventional method into convex micro-tablets with a gross mass of 10.0 mg and a diameter of 2.0 mm. Instead of this classic tabletting method other methods for making tablets such as direct tabletting or solid dispersions by the melt method and the spray drying method may also be used.

The gastric acid-resistant coating may be poured or sprayed on in a classic coating pan or applied in a fluidised-bed apparatus. In order to achieve resistance to gastric acid, portions of a solution of 2.250 kg of hydroxy propyl methyl cellulose phthalate (HPMCP, Pharmacoat HP 50) are dissolved in a mixture of the following solvents: acetone 13.00 l, ethanol 94% weight denatured with 2% ketone 13.50 l and demineralised water 2.50 l. 0.240 kg of castor oil are added as softening agent to the finished solution and applied in portions to the tablet cores in the usual manner.

Film-coat: After drying is completed, a suspension of the following composition is applied as a film-coat in the same apparatus: talcum 0.340 kg, titanium (VI) oxide Cronus RN 56 0.400 kg, coloured lacquer L red lacquer 86837 0.324 kg, Eudragit E 12.5% 4.800 kg and polyethylene glycol 6000 pH 11 XI 0.120 kg in a solvent mixture of the following composition: 2-propanol 8.170 kg, aqua demineralisata 0.200 kg and glycerine triacetate (Triacetin) 0.600 kg.

The gastric acid-resistant micro-tablets are then filled into hard gelatine capsules at a net weight of 500.0 mg and sealed.

Example 5

Preparation of enteric-coated film tablets containing 67.0 mg of monoethyl fumarate-Ca salt, 30.0 mg of dimethyl fumarate, 5.0 mg of monoethyl fumarate-Mg salt and 3.0 mg of monoethyl fumarate-Zn salt, which corresponds to 75 mg of fumaric acids ("mite" tablets)

Taking the necessary precautions (breathing mask, gloves, protective clothing, etc.), 3.000 kg of dimethyl fumarate, 6.700 kg of monoethyl fumarate-Ca salt, 0.500 kg of monoethyl fumarate-Mg salt and 0,300 kg of monoethyl fumarate-Zn salt are homogenised by means of an 800 sieve. An excipient mixture of the following composition is prepared in a similar manner to example 4, namely 30.000 kg of starch derivative (STA-RX 1500®), 3.000 kg of micro-crystalline cellulose (Avicel PH 101), 0.750 kg of polyvinyl pyrrolidone (PVP, Kollidon® 25), 4.000 kg of Primogel, 0.250 kg of colloidal silicic acid (Aerosil®). The excipients and the mixture of active ingredients are mixed intimately and homogenised by means of a 200 sieve. With the aid of a 2% aqueous solution of polyvinyl pyrrolidone (PVP, Kollidon® 25), the mass is processed in the usual manner to obtain a binder granulate. A powder mixture of the following excipients is added to the dried granulate as an outer phase: 0.500 kg of Mg stearate (Ph. Eur.) and 0.800 kg of talcum (Ph. Eur. II).

The homogenous granulate mixture is pressed in the usual manner to obtain convex tablet cores having a weight of 500.0 mg and a diameter of 11.5 mm. In addition to binder methods other tabletting methods according to examples 1 and 4 may also be used. The application of a gastric acid-resistant coating and a film-coat to the tablet cores is described analogously in examples 1 and 4.

The compositions according to the invention are preferably administered perorally in the form of tablets or capsules. These solid single-dosage medicaments are preferably provided with a gastric acid-resistant coating which, once having passed the stomach, is dissolved within a few minutes by the juice present in the small intestine and releases the active ingredient from the medicament. At the beginning and at the end of systemic treatment a lower dosage (mite) is required, whereas higher dosages (forte) are suitable for a regimen after the initial phase.

In addition to compositions given orally in the form of capsules, granulates and tablets, preparations for cutaneous and transdermal administration in the form of ointments, plasters, lotions and shower compositions, preparations for parenteral administration in the form of aqueous micro-dispersions, oil-in-water emulsions or oily solutions, preparations for rectal administration in the form of suppositories or micro-enemas and preparations for a therapy of hair, finger-nails and toe-nails by medication are also the subject matter of the invention.

Example 6

Preparation of enteric-coated film-tablets containing 100.0 mg of monomethyl fumarate-Ca salt, which corresponds to 78 mg of fumaric acid Taking the necessary precautions (breathing mask, gloves, protective clothing, etc.), 10.000 kg of monomethyl fumarate calcium salt are crushed, mixed and homogenised by means of an 800 sieve. Then an excipient mixture with the following composition is prepared: 21.000 kg of starch derivative (STA-RX 1500®), 2.000 kg of micro-crystalline cellulose (Avicel PH 101®), 0.600 kg of polyvinyl pyrrolidone (PVP, Kollidon® 25) 4.000 kg of Primogel, 0.300 kg of colloidal silicic acid (Aerosil®). The active ingredient is added to the mixture, mixed, homogenised by means of a 200 sieve, processed in the usual manner with a 2% aqueous solution of polyvidon pyrrolidone (Kollidon® K30) to obtain a binder granulate and then mixed in the dry state with the outer phase. Said outer phase consists of 2.000 kg of a so-called FST-complex containing 80% of talcum, 10% of silicic acid and 10% of magnesium stearate. Then the mixture is pressed in the usual manner to obtain convex tablets having a weight of 400 mg and a diameter of 10 mm. Instead of these classic tabletting methods other methods for preparing tablets such as direct tabletting and solid dispersions according to the melting and spray-drying method may also be used. The application of a gastric acid-resistant coating and a film-coat to the tablet cores is carried out analogously to examples 1 and 4.

Example 7

Preparation of enteric-coated film-tablets containing 50.0 mg of monomethyl fumarate-Ca salt, 50.0 mg of dimethyl fumarate, 5.0 mg of monomethyl fumarate-Mg salt and 3.0 mg of monomethyl fumarate-Zn salt, which corresponds to 85 mg of fumaric acid Taking the necessary precautions (breathing mask, gloves, protective clothing, etc.), 5.000 kg of dimethyl fumarate, 5.000 kg of monomethyl fumarate-Ca salt, 0.500 kg of monomethyl fumarate-Mg salt and 0.300 kg of monomethyl fumarate-Zn salt are crushed, mixed and homogenised by means of an 800 sieve. Then an excipient mixture with the following composition is prepared as described in example 4: 19.000 kg of starch derivative (STA-RX 1500®), 3.000 kg of micro-crystalline cellulose (Avicel PH 101®), 0.750 kg of polyvinyl pyrrolidone (PVP, Kollidon® 120) 4.000 kg of Primogel, 0.250 kg of colloidal silicic acid (Aerosil®).

The excipients and the active ingredient are mixed intensely, homogenised by means of a 200 sieve, processed in the usual manner with a 2% aqueous solution of polyvinyl pyrrolidone (PVP, Kollidon® 25) to obtain a binder granulate and then mixed in the dry state with the outer phase. Said outer phase consists of 0.500 kg of magnesium stearate (Ph. Eur.) and 1.500 kg of talcum (Ph. Eur. II).

Then the entire granulate is pressed in the usual manner to obtain convex tablets having a weight of 400 mg and a diameter of 10 mm. Instead of these classic tabletting methods other methods for preparing tablets such as direct tabletting and solid dispersions according to the melting and spray-drying method may also be used. The application of a gastric acid-resistant coating and a film-coat to the tablet cores is carried out analogously to examples 1 and 4.

Example 8

Preparation of enteric-coated film-tablets containing 50.0 mg of mono-n-propyl fumarate-Ca salt, which corresponds to 32,8 mg of fumaric acid Taking the necessary precautions (breathing mask, gloves, protective clothing, etc.), 5.000 kg of mono-propyl fumarate-Ca salt are crushed, mixed and homogenised by means of an 800 sieve. Then an excipient mixture with the following composition is prepared: 25.000 kg of starch derivative (STA-RX 1500®), 3.000 kg of micro-crystalline cellulose (Avicel PH 101®), 0.600 kg of polyvinyl pyrrolidone (PVP, Kollidon® 25), 4.000 kg of Primogel, 0.300 kg of colloidal silicic acid (Aerosil®)

The active ingredient is added to the powder mixture, mixed, homogenised by means of a 200 sieve, processed in the usual manner with a 2% aqueous solution of polyvidon pyrrolidone (Kollidon® K30) to obtain a binder granulate and then mixed in the dry state with the outer phase. Said outer phase consists of 2.000 kg of a so-called FST-complex containing 80% of talcum, 10% of silicic acid and 10% of magnesium stearate.

Then the entire granulate is pressed in the usual manner to obtain convex tablets having a weight of 400 mg and a diameter of 10 mm. Instead of these classic tabletting methods other methods for preparing tablets such as direct tabletting and solid dispersions according to the melting and spray-drying method may also be used. The application of a gastric acid-resistant coating and a film-coat to the tablet cores is carried out analogously to examples 1 and 4.

Example 9

Preparation of gastric-acid resistant pellets in capsules containing 50.0 mg of monomethyl fumarate-Ca salt, 5.0 mg of monomethyl fumarate-Mg salt and 3.0 mg of monomethyl fumarate-Zn salt, which corresponds to 45 mg of fumaric acid Taking the necessary precautions (breathing mask, gloves, protective clothing, etc.), 5.000 kg of monomethyl fumarate-Ca salt, 0.500 kg of monomethyl fumarate-Mg salt and 0.300 kg of monomethyl fumarate-Zn salt are crushed, mixed intensely and homogenised by means of a 400 sieve. At the same time, 2 l of a 20% (m/V) polyvinyl pyrrolidone (Kollidon K30) solution in ethanol is prepared. 7.250 kg of non-pareilles pellets are placed in a coating pan and sprayed with part of the Kollidon K30 solution until slightly moist. Then the active ingredient mixture is added in portions until the pellets are dry. This moistening/drying procedure is continued until all of the active ingredient mixture has been added. The remainder of the PVP solution is mixed with 0.720 kg of Eudragit E 12.5% solution and sprayed onto the pellets in its entirety. Finally, the pellets are moved around until completely dry. Instead of this method, other methods for preparing pellets may also be used, such as fluidised-bed coating or the extrusion-spherosination method. In addition, pellets containing the individual active ingredients may be prepared and then added in appropriate proportions after having been provided with a film-coat (see below).

The pellets are sprayed with Eudragit S 12.5% solution and dried with talcum. After each spraying/drying cycle the release of the active ingredient is measured and the addition of Eudragit S 12.5% solution/talcum continued until the release values meet the specification.

Then the enteric-coated pellets are filled into capsules (146 mg pellets/capsule).

Example 10

Preparation of gastric-acid resistant capsules containing 50.0 mg of mono-iso-propyl fumarate-Ca salt, 50.0 mg of di-iso-propyl fumarate, 5.0 mg of mono-iso-propyl fumarate-Mg salt and 3.0 mg of mono-iso-propyl fumarate-Zn salt, which corresponds to 67 mg of fumaric acid Taking the necessary precautions (breathing mask, gloves, protective clothing, etc.), 5.000 kg of mono-isopropyl fumarate-Ca salt, 5.000 kg of di-iso-propyl fumarate, 0.500 kg of mono-iso-propyl fumarate-Mg salt and 0.300 kg of mono-iso-propyl fumarate-Zn salt are crushed, mixed intensely and homogenised by means of an 800 sieve. Then a powder mixture with the following composition is mixed into this active ingredient mixture: 32.200 kg of spray-dried lactose, 2.000 kg of micro-crystalline cellulose (Avicel) and 1.000 kg of colloidal silicic acid (Aerosil®), 1.000 kg of magnesium stearate and 2.000 kg of talcum. The entire powder mixture is homogenised once more by means of a 200 sieve, filled into hard gelatine capsules at a net weight of 500 mg and saled.

These capsules are then usually provided with a enteric-coated coating consisting of hydroxy propyl methyl cellulose phthalate (HPMCP) and castor oil as softening agent. Instead of hard gelatine capsules, the active ingredient may also be filled into other gastric acid-resistant capsules which consist of a mixture of cellulose acetate phthalate (CAP) and hydroxy propyl ethyl cellulose acetate phthalate (HPMCP).

Example 11

Preparation of micro-pellets in capsules containing 50.0 mg of methyl hydrogen fumarate, which corresponds to a total of 44.6 mg of fumaric acid Taking the necessary precautions (breathing mask, gloves, protective clothing, etc.), 5.000 kg of methyl hydrogen fumarate are crushed and homogenised by means of a 400 sieve. In addition, 2 l of a 20% (m/V) polyvinyl pyrrolidone (Kollidon K30) solution in ethanol are prepared. 7.250 kg of non-pareilles pellets are placed into a coating pan and sprayed with part of the Kollidon K30 solution until slightly moist. Then the active ingredient mixture is added in portions until the pellets are dry. This moistening/drying cycle is continued until all of the active ingredient mixture has been added. Finally, the pellets are moved around until they are completely dry. Instead of this method, it is also possible to use other methods for preparing pellets, such as fluidised-bed coating and the extrusion/spherosination method. In addition, the pellets may also be prepared with the individual active ingredients which are then added in the appropriate proportion after film-coating.

Then the pellets are filled in capsules (126.5 mg of pellets/capsule).

In the following, the effectiveness of the use according to the invention is shown on the example of the inhibition of haemagglutinin formation in an animal experiment and compared with a recognised medicament of the prior art:

Investigation of the influence of a formulation according to example 4 and of methyl hydrogen fumarate-Ca salt on haemagglutinin formation in mice after peroral administration By inhibiting the formation of haemagglutinin in mice immuno-suppressive effects of certain substances may be shown. This test is based on the direct haemagglutination where a visible agglutination of erythrocytes occurs due to specific antibodies directed against the surface antigens of erythrocytes.

Mice are made immune with sheep erythrocytes (day 0). Then the substance to be tested is applied five times (days 0–4). On the ninth day after immunisation, the haemagglutinin levels are determined. A reduction in haemagglutinin formation shows an immuno-suppressive effect.

It was the objective of these tests to test the effect of a formulation according to example 4 and of methyl hydrogen fumarate-Ca salt on the haemagglutinin formation in mice after peroral administration of 150, 300 and 600 mg/kg, respectively.

In this experiment, it was possible to show the dosage-dependent suppressive effect of the formulation on the basis of the proportions of the active ingredients according to example 4 on haemagglutinin formation in mice. The effect of a total dose of 300 mg/kg of said formulation (application of the combination of active ingredients in a 0.8% suspension in aqueous HPMC of gel-like consistency) was still in the normal range of deviation, whereas a reproducible 29% inhibition of haemagglutinin formation could be shown after administration of 600 mg/kg of the above formulation.

A dosage-dependent suppressive effect on haemagglutinin formation in mice could also be shown for methyl hydrogen fumarate-Ca salt. A dosage of 300 mg/kg of methyl hydrogen fumarate-Ca salt caused a slight reduction of haemagglutinin formation, whereas a reproducible 38% inhibition of haemagglutinin formation could be shown after administration of 600 mg/kg methyl hydrogen fumarate-Ca salt.

For comparison, an analogous experiment was carried out in a dosage range of 150, 200 and 300 mg/kg of cyclosporin A. The dosage range was selected in accordance with J. B. Borel et al., Biological Effects of Cyclosporin A: A New Antilymphotic Agent, Biological and Medical Research Division, Sandoz Ltd., CH-4002 Basle, Switzerland; Agents and Actions, 6/4, 468–475 (1975). For cyclosporin, a 37% reduction in haemagglutinin formation could be shown at a dosage of 150 mg/kg. At a maximum dosage of 300 mg/kg of cyclosporin, a 59% inhibition of haemagglutinin formation was achieved.

The results of these investigations permit the conclusion that both a formulation according to example 4 and methyl hydrogen fumarate-Ca salt exercise a significant immuno-suppressive effect.

Among other things, the immuno-suppressive effect of cyclosporin is caused by an inhibition of Th-1 cell formation. As in vitro experiments have shown, fumarates cause a shift in the cytokin pattern from the Th1 to the Th2 type.

If the findings of both the in vivo and the in vitro experiments are viewed together, a meaningful and unexpectedly improved use of fumarates in transplantation medicine, especially with regard to a long-term maintnance therapy results.

Investigation of the influence of a formulation according to example 4 and methyl hydrogen fumarate-Ca salt after peroral administration on haemagglutinin formation in mice Reduction of serum haemagglutinin formation in mice

| mg/kg bodyweight p.o. | Proportion of the serum titres control/verum group | Suppression index | Inhibition of haemagglutinin formation in % |
|---|---|---|---|
| Combination of active ingredients as in example 4 | | | |
| 150 | 10.7/12.8 | 0.84 | 16 |
| 300 | 10.8/12.8 | 0.84 | 16 |
| 600 | 9.1/12.8 | 0.71 | 29 |

-continued

| mg/kg bodyweight p.o. | Proportion of the serum titres control/verum group | Suppression index | Inhibition of haemagglutinin formation in % |
|---|---|---|---|
| Methyl hydrogen fumarate-Ca salt | | | |
| 150 | 11.1/12.8 | 0.87 | 13 |
| 300 | 10.2/12.8 | 0.80 | 20 |
| 600 | 7.9/12.8 | 0.62 | 38 |
| Cyclosporin A | | | |
| 150 | 8.0/12.8 | 0.63 | 37 |
| 200 | 7.1/12.8 | 0.55 | 45 |
| 300 | 5.3/12.8 | 0.41 | 59 | p.o. = administered perorally

Haemagglutinins

Designation for substances causing haemagglutination, especially agglutinating antibodies, phythaemagglutinins, generally haemagglutinins formed by virus infection (measles, mumps, rubella, influenza, arboviroses) and surface antigens of certain virus types.

Haemagglutination

Visible agglutination of erythrocytes caused by haemagglutinins; as direct (active) haemagglutination caused by antibodies directed specifically against surface antigens of the erythrocytes or as indirect (passive) haemagglutination after loading erythrocytes with an antigen (e.g. Vi-antigen in typhus-Vi-haemagglutination, globulin in an anti-globulin test) caused by antibodies directed specifically against the relevant antigen. The strength of a haemagglutination (for example in a serological titration of a haemagglutinating anti-serum) is reported by a numeral (dilution stage of the serum tested where a haemagglutination can only just be detected).

Compared to a therapy with substances of the prior art such as cyclosporin which may cause severe kidney disorders or diseases of the lymphoproliferative system, treatment with fumaric acid derivatives according to the indications as per the invention will cause only temporary disorders and will rarely have severe side effects [cf. DMW (German Weekly Medical Magazine), 121 (1996) pages 1605–1607]. Especially in view of the necessary long-term therapy and prevention of graft-versus-host reactions or multiple sclerosis this unexpected effect of the use according to the invention is of the highest interest. Combination therapy of cyclosporin with the fumaric acid derivatives will reduce the toxic side effects of the former compounds dramatically and unexpectedly. Moreover, the use according to the invention is also of major significance in the substitution of a corticoid therapy which, as is generally known, has severe side effects.

The terms and expressions which have been employed are used as terms of description and not of limitation, and there is no intention in the use of such terms and expressions of excluding any equivalent of the features shown and described or portions thereof, it being recognized that various modifications are possible within the scope of the invention.

What is claimed is:

1. A method for treating a patient suffering from an auto immune disease selected from the group consisting of graft-versus host reactions, juvenile diabetes, Hashimoto's thyroiditis, Grave's disease, systemic Lupus erythematosus (SLE), Sjogren's syndrome, pernicious anaemia and chronically active (=lupoid) hepatitis comprising: administering an effective amount of a compound of a sodium, potassium, calcium, magnesium, zinc or iron salt of a funaric acid monoalkyl ester of the general formula

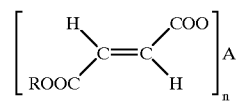

optionally in combination with dialkyl fumarate of the formula

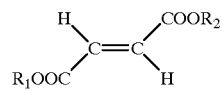

wherein A is a bivalent cation selected from the group consisting of Ca, Mg, Zn or Fe or a monovalent cation from the series consisting of potassium or sodium, respectively, and n denotes the numeral 1 or 2 depending on the type of cation, or administering at least one alkyl hydrogen fumarate compound of the general formula

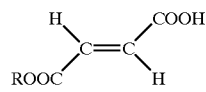

optionally in combination with dialkyl fumarate of the formula

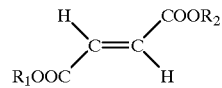

wherein each of R, $R_1$ and $R_2$ is $C_1$–$C_5$ alkyl and may be the same or different; and optionally, in combination with commonly used pharmaceutical excipients and vehicles.

2. The method of claim 1, wherein the calcium salt of the fumaric acid monoethyl ester is administered.

3. The method of claim 1, wherein the calcium salt of the fumaric acid monomethyl ester is administered.

4. The method of claim 1, wherein the calcium salt of the fumaric acid monoethyl ester in admixture with dimethyl fumarate is administered.

5. The method of claim 1, wherein the calcium and zinc salts of the fumaric acid monoethyl ester in admixture with dimethyl fumarate are administered.

6. The method of claim 1, wherein a mixture of calcium, magnesium and zinc salt of the fumaric acid monoethyl ester in admixture with dimethyl fumarate is administered.

7. The method of claim 1, wherein the method for treating comprises oral administration in the form of tablets or capsules, said tablets or capsules comprising the calcium salt of the fumaric acid monoalkyl ester in an amount of 10 to 300 mg, the total weight of the active ingredients being 10 to 300 mg.

8. The method of claim 1, wherein the method for treating comprises oral administration in the form of tablets or capsules, said tablets or capsules comprising 10 to 290 parts by weight of the calcium salt of the fumaric acid monoalkyl ester and 290 to 10 parts by weight of dimethyl fumarate, the total weight of the active ingredients being 20 to 300 mg.

9. The method of claim 1, wherein the method for treating comprises oral administration in the form of tablets or capsules, said tablets or capsules comprising 10 to 250 parts by weight of the calcium salt of the fumaric acid monoalkyl ester, 1 to 50 parts by weight of dimethyl fumarate and 1 to 50 parts by weight of the zinc salt of the fumaric acid monoalkyl ester, the total weight of the active ingredients being 20 to 300 mg.

10. The method of claim 1, wherein the method for treating comprises oral administration of a pharmaceutical composition in the form of tablets or capsules comprising 10 to 250 parts by weight of the calcium salt of the fumaric acid monoalky ester, 250 to 10 parts by weight of dimethyl fumarate, 1 to 50 parts by weight of the magnesium salt of the fumaric acid monoalkyl ester and 1 to 50 parts by weight of the zinc salt of the fumaric acid monoalkyl ester, the total weight of the active ingredients being 30 to 300 mg.

11. The method of claim 1, further comprising a sequential or alternating administration of cyclosporin.

12. The method of claim 1, wherein the compound is contained in pellets or microtablets having a mean diameter, respectively, in the range of 300 to 2,000 μm, especially in the range of 500 μm to 1,500 μm or 1,000 μm.

13. The method of claim 1, wherein the compound is administered as a medicament in the form of tablets, soft or hard gelatine capsules, granules, micro-tablets and in the form of preparations which may be applied by topical, parenteral and rectal routes.

14. The method for claim 1, wherein the dosage unit of the medicament is coated with a gastric acid resistant coating.

15. A method for treating a patient suffering from an auto immune disease selected from the group consisting of polyarthritis, multiple sclerosis and graft-versus host reactions, juvenile diabetes, Hashimoto's thyroiditis, Grave's disease, systemic Lupus erythematosus (SLE), Sjogren's syndrome, pernicious anaemia and chronically active (=lupoid) hepatitis comprising:

administering in the form of pellets or microtablets an effective amount of a compound of a sodium potassium, calcium, magnesium, zinc or iron salt of a fumaric acid monoalkyl ester of the general formula:

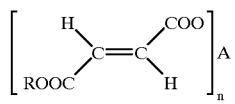

optionally in combination with dialkyl funarate of the formula

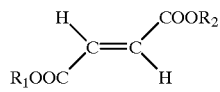

wherein A is a bivalent cation selected from the group consisting of Ca, Mg, Zn or Fe or a monovalent cation from the series consisting of potassium or sodium, respectively, and n denotes the numeral 1 or 2 depending on the type of cation, or administering at least one alkyl hydrogen fumarate compound of the general formula

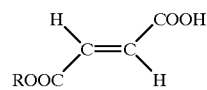

optionally in combination with dialkyl fumarate of the formula

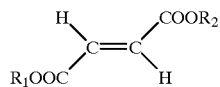

wherein each of R, $R_1$ and $R_2$ is $C_1$–$C_5$ alkyl and may be the same or different.

16. The method of claim 15, wherein the calcium salt of the fumaric acid monoethyl ester is administered.

17. The method of claim 15, wherein the calcium salt of the fumaric acid monomethyl ester is administered.

18. The method of claim 15, wherein the calcium salt of the fumaric acid monoethyl ester in admixture with dimethyl fumarate is administered.

19. The method of claim 15, wherein the calcium and zinc salts of the fumaric acid monoethyl ester in admixture with dimethyl fumarate are administered.

20. The method of claim 15, wherein a mixture of calcium, magnesium and zinc salts of the fumaric acid monoethyl ester in admixture with dimethyl fumarate is administered.

21. The method of claim 15, further comprising a sequential or alternating administration of cyclosporin.

22. The method of claim 15, wherein the dosage unit of the medicament is coated with a gastric acid resistant coating.

23. The method of claim 15, wherein the size of the microtablets or pellets is in the range of 300 μm to 200 μm.

* * * * *

UNITED STATES PATENT AND TRADEMARK OFFICE
CERTIFICATE OF CORRECTION

PATENT NO. : 6,436,992 B1
DATED : August 20, 2002
INVENTOR(S) : Rajendra Kumar Joshi It is certified that error appears in the above-identified patent and that said Letters Patent is hereby corrected as shown below:

<u>Column 16,</u>
Lines 48-49, should read as follows:

-- 23. The method of claim 15, wherein the size of the microtablets or pellets is in the range of 300μm to 2000μm. --.

Signed and Sealed this

Seventh Day of September, 2004

JON W. DUDAS
*Director of the United States Patent and Trademark Office*